(12) United States Patent
Bailey et al.

(10) Patent No.: US 7,462,370 B2
(45) Date of Patent: Dec. 9, 2008

(54) COMPOSITIONS ENRICHED IN ANTHOCYANINS

(75) Inventors: David T. Bailey, Boulder, CO (US); Delano R. Freeberg, Coralville, IA (US); Dennis Gertenbach, Boulder, CO (US); Gerald T. Gourdin, Boulder, CO (US); Steven L. Richheimer, Westminster, CO (US); Michael S. Tempesta, El Granada, CA (US); F. Joseph Daugherty, Omaha, NE (US)

(73) Assignee: Phenolics, LLC, Omaha, NE (US)

( * ) Notice: Subject to any disclaimer, the term of this patent is extended or adjusted under 35 U.S.C. 154(b) by 0 days.

(21) Appl. No.: 11/750,906

(22) Filed: May 18, 2007

(65) Prior Publication Data

US 2007/0269536 A1    Nov. 22, 2007

Related U.S. Application Data

(63) Continuation of application No. 10/893,138, filed on Jul. 15, 2004, now abandoned, which is a continuation of application No. 09/943,158, filed on Aug. 30, 2001, now Pat. No. 6,780,442.

(60) Provisional application No. 60/229,205, filed on Aug. 31, 2000.

(51) Int. Cl.
*A61K 36/45* (2006.01)
(52) U.S. Cl. ...................................... 424/732
(58) Field of Classification Search ................ 424/732; 514/27, 456
See application file for complete search history.

(56) References Cited

U.S. PATENT DOCUMENTS

| 4,413,004 | A | 11/1983 | Lietti et al. |
| 4,452,822 | A | 6/1984 | Shrikhande |
| 4,481,226 | A | 11/1984 | Crosby et al. |
| 4,500,556 | A | 2/1985 | Langston |
| 4,857,327 | A | 8/1989 | Virdalm |
| 4,863,956 | A | 9/1989 | Gabetta et al. |
| 5,200,186 | A | 4/1993 | Gabetta et al. |
| 5,211,944 | A | 5/1993 | Tempesta |
| 5,494,661 | A | 2/1996 | Tempesta |
| 5,525,341 | A | 6/1996 | Walker et al. |
| 5,646,178 | A | 7/1997 | Walker et al. |
| 5,773,262 | A | 6/1998 | Ariga et al. |
| 5,780,060 | A | 7/1998 | Levy et al. |
| 5,804,597 | A | 9/1998 | Yamakoshi et al. |

(Continued)

FOREIGN PATENT DOCUMENTS

DE        3027933        2/1981

(Continued)

OTHER PUBLICATIONS

Lisa Rapport, Brian Lockwood; "(6) Proanthocyanidins and Grape Seed Extract,"; The Pharmaceutical Journal; Apr. 28, 2001; pp. 581-584; vol. 266.

(Continued)

*Primary Examiner*—Taylor Victor Oh
(74) *Attorney, Agent, or Firm*—Hogan & Hartson LLP (57) ABSTRACT

This invention provides compositions enriched for anthocyanins and methods of preparation thereof from a crude plant extract. The method of preparation includes a novel column purification step using a brominated polystyrene resin.

2 Claims, 6 Drawing Sheets

U.S. PATENT DOCUMENTS

| | | | |
|---|---|---|---|
| 5,886,029 | A | 3/1999 | Dhaliwal |
| 5,908,650 | A | 6/1999 | Lenoble et al. |
| 5,912,363 | A | 6/1999 | Nafisi-Movaghar et al. |
| 5,968,517 | A | 10/1999 | Duncan et al. |
| 6,099,854 | A | 8/2000 | Howard et al. |
| 6,103,756 | A | 8/2000 | Gorsek |
| 6,194,469 | B1 | 2/2001 | Nair et al. |
| 6,200,569 | B1 | 3/2001 | Cheng |
| 6,210,681 | B1 | 4/2001 | Walker et al. |

FOREIGN PATENT DOCUMENTS

| | | | |
|---|---|---|---|
| EP | | 573777 A1 | 12/1993 |
| GB | | 1235379 | 6/1971 |
| WO | WO 02/17732 A2 | | 3/2002 |

OTHER PUBLICATIONS

L. Gao and G. Mazza, Characterization, Quantitation, and Distribution of Anthocyanins and Colorless Phenolics in Sweet Cherries, Journal of Agricultural and Food Chemistry 48 (2) pp. 343-346.

M. Azar, E. Verette, and S. Brun, "Identification of Some Phenolic Compounds in Billberry Juice *Vaccinium myrtillus*," Journal of Food Science, vol. 52, No. 5 (1987) pp. 1255-1257.

D.L. Madhavi, S. Juthangkoon, K. Lewen, M.D., Berber-Jimenez, M.A.L. Smith, "Characterization of Anthocyanins from *Ajuga pyramidalis* Metallica Crispa Cell Cultures," J. Agric. Food Chem, vol. 44, No. 4, (1996) pp. 1170-1176.

Elliott Middleton, Jr., "Effect of Plant Flavonoids on Immune and Inflammatory Cell Function," Flavonoids in the Living Systems (1998) pp. 175-182.

L. Yeap Foo, Yinrong Lu, Amy B. Howell and Nicholi Vorsa, A-Type Proanthocyanindin Trimers from Cranberry that Inhibit Adherence of Uropathogenic P-Fimbriated *Escherichia coli* J. Nat. Prod., vol. 63 (9) (2000) pp. 1225-1228.

Lai Yep Foo, Yinrong Lu, Amy B. Howell, Nicholi Vorsa, "The structure of cranberry proanthocyanidins which inhibit adherence of uropathogenic P-fimbriated *Escherichia coli* in vitro," Photochemistry, vol. 54, pp. 173-181. (2000).

Ronald L. Prior, Sheryl A. Lazarus, et al., "Identification of Procyanindins and Anthocyanins in Blueberries and Cranberries (Vaccinium Spp.) Using High-Performance Liquid Chromatography/Mass Spectrometry", LC/MS Analyses of Procyanidins in Vaccinium Spp., pp. A-G.

Horotoshi Tamura and Atsushi Yamagami, "Antioxidative Activity of Monoacylated Anthocyanins Isolated from Muscat Baily A Grape," J.Argic. Food Chem, 1994, 42, 1612-1615.

Ronald L. Prior, Guohua Cao, Antonio Martin, Emin Scofic, et al., "Antioxidant Capacity As Influenced by Total Phenolic and Anthocyanin Content, Maturity, and Variety of Vaccinium Species," J. Agric Food Chem, 1988, vol. 46, pp. 2686-2693.

Geza Hrazdina, "Column Chromatographic Isolation of the Anthocyanidin-3, 5-Diglucosides from Grapes," J. Agr Food Chem., vol. 18, No. 2, 1970, pp. 243-245.

Sterling. "Proanthocyanidin Power" [online]; [retrieved on May 1, 2002]. http://www.healthwellexchange.com/nutritionsciencenews/nsn_backs/Jun_00/proantho.cfm.

M. Sterling, "Got Anthocyanins?" [online], [retrieved on Feb. 28, 2002]. http://www.healthwatchexchange.com/nutritionsciencenews/nsn_backs/Dec_01/antho.cfm.

M. Sterling, Proanthocyanindin Power [online], [retrieved on Feb. 28, 2002]. Retrieved from the http:/www.healthwellexchange.com/nutritionsciencenews/nsn_backs/Jun_00/proantho.cfm.

A.M. Fine. "Oligomeric Proanthocyanidin Complexes: History, Structure, and Phytopharmaceutical Applications", [online], [retrieved on Feb. 28, 2002]. Retrieved from the Internet URL: http://ww.thorne.com/almedrev/fulltext./oligo5-2.html.

"Oligomeric Proanthocyanidins (Pycnogenols)" [online]; [retrieved on May 1, 2002]. Retrieved from the Internet URL http://www.thorne.com/pycnogenols.html.

International Search Report, PCT/US01/27107, Feb. 1, 2002.

EP Search Report, EP 26831, Dec. 30, 2003.

A. Lietti, et al., "Studies on *Vaccinium myrtillus* anthocyanosides", Arsniemittle Forschung, Drug Research, 1976, 26(5): 829-832.

PCT International Search Report PCT/US05/24003.

Anderson, et al. " Isolation and Characterization of Polyphenol Type-A Polymers from Cinnamon with Insulin-like Biological Activity"; Journal of Agricultural and Food Chemistry; 2004; pp. 65-70; vol. 52, No. 1; American Chemical Society.

Internet Website http://www.herbsmd.com/shop/xq/asp/pid/8505/qx/productdetail.asp Thermogenic Fat Burners by Weider; pp. 1-2.

R. Ubillas, S.D. Jolad, et al., "SP-303 and Antiviral Oligomeric Proanthocyanidin from the Latex of Croton lechleri (Sange de Drago)," Phytomedicine vol. 1, pp. 77-106 (1994).

COMPOSITIONS ENRICHED IN ANTHOCYANINS

RELATED APPLICATIONS

The present application is a continuation of U.S. patent application Ser. No. 10/893,138 filed Jul. 15, 2004, which is a continuation application of U.S. patent application Ser. No. 09/943,158 filed Aug. 30, 2001 (now U.S. Pat. No. 6,780,442), which claims priority to U.S. Provisional Ser. No. 60/229,205, filed Aug. 31, 2000, all of which are incorporated herein by reference in their entireties.

BACKGROUND OF THE INVENTION

1. Field of the Invention

The present invention is directed to efficient one- or two-step processes for producing compositions enriched in phenols from dried or fresh plant material. More particularly, the present invention provides methods for producing compositions enriched for anthocyanins and proanthocyanins.

2. Description of the Prior Art

Anthocyanins are naturally occurring compounds that are responsible for the red, purple, and blue colors of many fruits, vegetables, cereal grains, and flowers. For example, the colors of berry fruits, such as blueberries, bilberries, strawberries, raspberries, boysenberries, marionberries, cranberries, are due to many different anthocyanins. Over 300 structurally distinct anthocyanins have been identified in nature. Because anthocyanins are naturally occurring, they have attracted much interest for use as colorants for foods and beverages.

Recently, the interest in anthocyanin pigments has intensified because of their possible health benefits as dietary antioxidants. For example, anthocyanin pigments of bilberries (*Vaccinium myrtillus*) have long been used for improving visual acuity and treating circulatory disorders. There is experimental evidence that certain anthocyanins and flavonoids have anti-inflammatory properties. In addition, there are reports that orally administered anthocyanins are beneficial for treating diabetes and ulcers and may have antiviral and antimicrobial activities. The chemical basis for these desirable properties of flavonoids is believed to be related to their antioxidant capacity. Thus, the antioxidant characteristics associated with berries and other fruits and vegetables have been attributed to their anthocyanin content.

Proanthocyanins are another class of flavonoid compounds that are found in fruits and vegetables and, while being colorless, have antioxidant activities.

Due to the above characteristics and benefits of anthocyanins and proanthocyanins, much effort has been put forth towards extracting these compounds from fruits, vegetables, and other plant sources. In addition to anthocyanins, plants, fruits, and vegetables also contain other compounds such as mineral salts, common organic acids such as citric or tartaric acid, carbohydrates, flavonoid glycosides and catechins. It is often desirable to isolate the anthocyanins and proanthocyanins from these compounds. Anthocyanins have been extracted from plants and fruits by various procedures. One extraction method of extracting anthocyanins employs sulfur dioxide. The extract is passed through an ion exchange column to adsorb the anthocyanin materials, and the adsorbed anthocyanins are eluted with acetone, alkali, or dimethyl formamide (DMF). Disadvantages of this process include the presence of sulfur dioxide, which interferes with adsorption of anthocyanins, thereby requiring multiple column adsorptions. Elution with alkali degrades the anthocyanins considerably, while DMF is not a recognized food additive and therefore complete removal of DMF from anthocyanins must be accomplished before the anthocyanins can be added to any food products.

Shrikhande, in U.S. Pat. No. 4,452,822, discloses a method for the production of a red coloring material for use as a colorant for food and beverages, wherein an anthocyanin-containing vegetable source material is extracted with sulfur dioxide to form an extract of anthocyanin material. The extract is first enzymatically treated to reduce or eliminate solid material present in the extract, and then treated by oxidizing the sulfur dioxide with hydrogen peroxide. After reducing the pH, the extract is loaded onto an ion exchange medium (a copolymer of styrene and divinyl benzene polymer or crosslinked polymethacrylate) that adsorbs the anthocyanins. However, it is very difficult to remove all the sulfur once it has been introduced. Further, hydrogen peroxide degrades the anthocyanins in the final product.

Gabetta, et al., in U.S. Pat. No. 5,200,186, disclose a process for the preparation of extracts with high content in anthocyanosides that involves treating a crude extract with bisulfite ions to provide anthocyanin-bisulfite adducts. After adjusting the pH of the extract to 5-6 by the addition of an aqueous alkali, the extract is loaded onto a non-polar polystyrene resin and the anthocyanin-bisulfite adducts are eluted. The obtained solution is extracted multiple times with butanol or amyl alcohol. After concentration and acidification (pH 1-2) of the organic phase, the extract with high anthocyanin content is isolated by lyophilization, or by precipitation with an aprotic solvent such as ethyl acetate. Again, it is difficult to remove all the sulfur once it has been introduced. In addition, it is difficult to remove the butanol, amyl alcohol, or ethyl acetate once these solvents are introduced.

Langston, in U.S. Pat. No. 4,500,556, discloses a method of producing an anthocyanin colorant from grape pomace by contacting an aqueous extraction solvent containing bisulfite ions to extract an anthocyanin-bisulfite ion adduct. The extract is then contacted with a nonionic adsorbent to adsorb the anthocyanin-bisulfite adduct, and the adsorbent is washed to remove soluble sugars, organic acids and other water soluble non-pigmented materials. The anthocyanins are then eluted from the adsorbent with an acidified organic solvent. Again, it is difficult to remove all the sulfur once it has been introduced.

Lietti, in U.S. Pat. No. 4,413,004, discloses a method of extracting anthocyanins from bilberry by extracting the fruit with anhydrous methanol containing hydrochloric acid, followed by adding lead acetate to precipitate the anthocyanins as the lead salts. However, the use of lead makes the products obtained by this process unsuitable for food use.

The above examples describe some processes known in the art for extracting and isolating anthocyanins from various plant materials. However, each of the above processes involves the use of toxic and/or environmentally hazardous materials. Consequently, the currant methods available for isolating and purifying anthocyanins are not easily scaled up to an efficient commercial process where disposal consideration of various chemicals and solvents play an important role in the overall feasibility of the process. Further, anthocyanins must be isolated in a manner which minimizes their natural instability toward degradation.

There is still a need, therefore, for an efficient process for isolating and purifying compositions containing anthocyanins for uses in nutraceuticals and pharmaceuticals that is cost-effective, scalable, economically sound, does not require the use of toxic solvents or reagents, and isolates the anthocyanins in a manner that minimizes their instability toward degradation.

SUMMARY OF THE INVENTION

Accordingly, the present invention provides simplified and economic methods for the extraction, isolation, and purification of compositions enriched for anthocyanins. More specifically, one aspect of this invention provides a method of preparing compositions enriched for anthyocyanins comprising: (a) extracting plants or plant parts known to contain anthocyanins to form a crude extract comprising anthocyanins and extraneous compounds; (b) adding a source of bisulfite ($HSO_3^-$) ions to form a sulfited extract containing anthocyanin-bisulfite adducts; (c) filtering the sulfited extract; (d) contacting the sulfited extract with a first resin which retains a portion of the extraneous materials; (e) washing the anthocyanin-bisulfite adducts from the resin; (f) acidifying the partially purified extract washed from the first resin to free the anthocyanins from anthocyanin-bisulfite adducts; (g) contacting the acidified extract with a brominated polystyrene resin which adsorbs the anthocyanins but does not retain the remaining extraneous materials; and (h) eluting the anthocyanins from the brominated polystyrene resin to obtain an extract enriched for anthocyanins.

This invention further provides methods for preparing compositions enriched for anthocyanins and proanthocyanins useful as nutraceuticals and pharmaceuticals. More specifically, one aspect of this invention provides a method of preparing compositions enriched for anthocyanins and proanthocyanins comprising: (a) extracting plants or plant parts known to contain anthocyanins with an acidified extraction solvent to form a crude extract comprising anthocyanins and extraneous compounds; (b) filtering the crude extract; contacting the filtered crude extract with a brominated polystyrene resin which adsorbs the anthocyanins but does not retain extraneous materials; and (c) eluting the anthocyanins from the brominated polystyrene resin to obtain an extract enriched for anthocyanins.

This invention further provides anthocyanin-enriched compositions isolated by the methods of this invention. The compositions are useful as nutraceuticals and pharmaceuticals.

The foregoing and other features, utilities and advantages of the invention will be apparent from the following more particular descriptions of preferred embodiments of the invention and as illustrated in the accompanying drawings and as particularly pointed out in the appended claims.

BRIEF DESCRIPTION OF THE DRAWINGS

The accompanying drawings, which are incorporated herein and form a part of the specification, illustrate preferred embodiments of the present invention, and together with the description, serve to explain the principles of the invention.

In the Drawings.

DETAILED DESCRIPTION OF THE INVENTION

The methods of this invention produce purified extracts and compositions enriched in anthocyanins from plant materials that naturally contain anthocyanins. The method of this invention further provide extracts and compositions enriched in total anthocyanins and proanthocyanins. As used herein, the term "extract" refers to a substance derived from a plant source that naturally contains anthocyanins, including extracts prepared from the whole plant or from various parts of the plant, such as the fruit, leaves, stems, roots, etc. Thus, the method of this invention is not limited to the particular part of the plant used to prepare the extract. In addition, the plant material may be fresh or dried plant material. Examples of plants and fruits that may be used in the preparation of the purified extracts of this invention include any plant, including fruits and vegetables, that contains anthocyanins, including blueberries, bilberries, blackberries, strawberries, red currants, black currants, cranberries, cherries, raspberries, grapes, currants, elderberries, hibiscus flowers, bell peppers, red cabbage, purple corn, and violet sweet potatoes. Most colored fruits and vegetables are known to contain anthocyanins.

The anthocyanin-enriched compositions described herein were assayed by standard spectrophotometric determination against a delphinidin chloride standard. Delphinidin chloride is an aglycone, whereas anthocyanins are glycosides (i.e., aglycones bound to one or more sugars). Therefore, the percent total anthocyanins given for the anthocyanin-enriched compositions described herein are actually given in terms of percent total aglycones. Consequently, as will be understood by those of skill in the art, the percentages of total anthocyanins (glycosides) in the anthocyanin-enriched compositions are actually at least 1.4 times greater than the measured total aglycones. Thus, as used throughout the specification and in the claims, the term "percent anthocyanins" refers to the percent total aglycones as determined against a delphinidin chloride standard, which measurement can be related to the total anthocyanins.

A. Two-Column Purification Process

Figure 1:
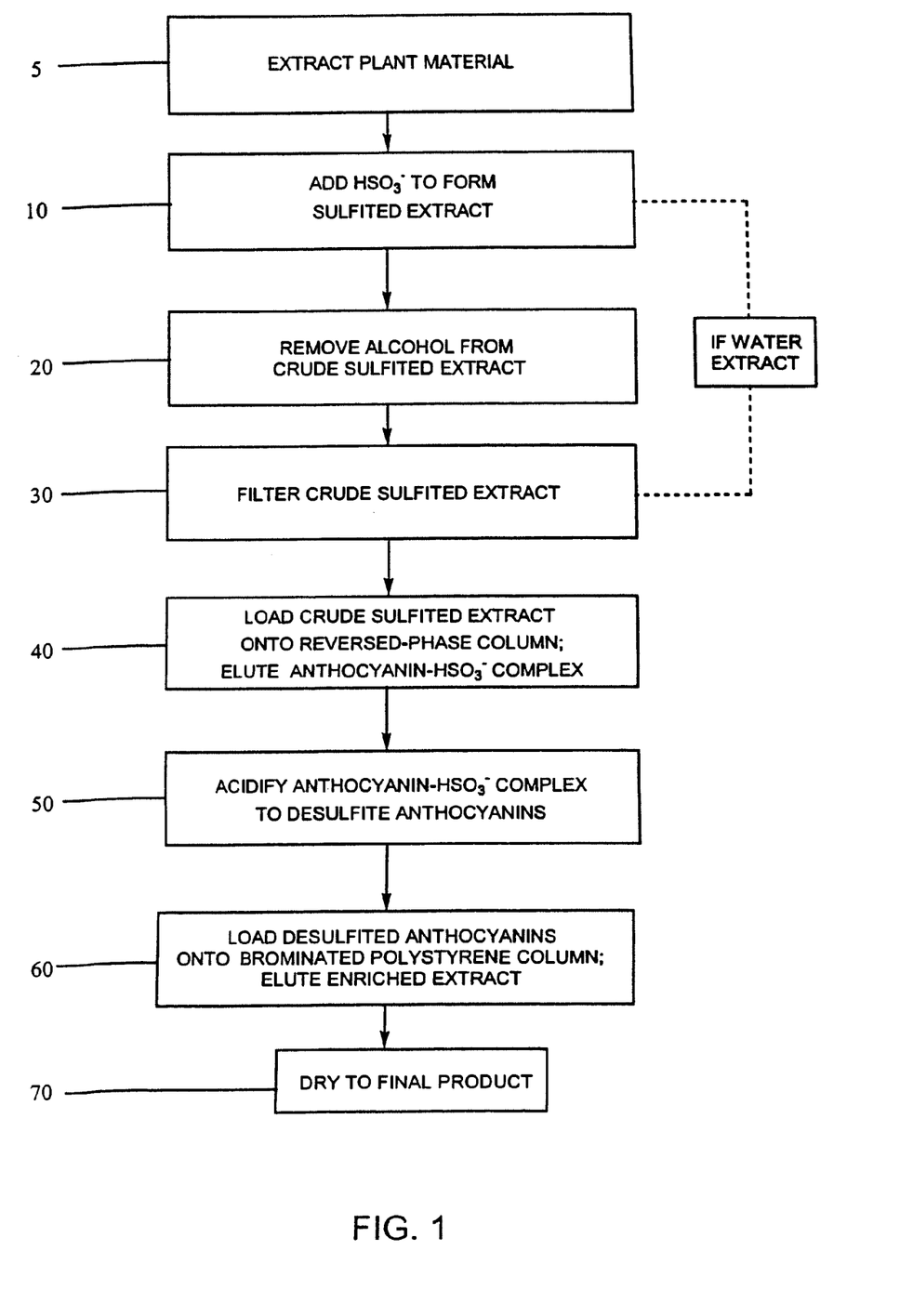
FIG. 1 is a flow chart for preparing an enriched extract according to one embodiment of this invention that comprises two separate purification steps using two different resins.

FIG. 1 is a flow chart showing the steps of one embodiment of this invention in which a purified extract of this invention enriched for anthocyanins may be prepared by a two-column purification process. The two-column purification process of this invention includes a novel step (step 60, FIG. 1) of purifying a partially purified extract using a brominated polystyrene resin. The method illustrated in FIG. 1 is based on the discovery that substituting a brominated polystyrene resin for the conventional polystyrene resin used in the art in the second column purification step (step 60) provides compositions having higher purities than with other polystyrene resins, as will be discussed below in detail.

Prior to the purification methods described herein, anthocyanins (typically along with proanthocyanins) are extracted from a plant material to form a crude extract (step 5, FIG. 1). The skilled person in this art will recognize that a variety of extraction methods are available in the literature, such as vat extraction, percolation, countercurrent extraction, etc. The particular method of extraction employed is not essential to the process of the present invention. The degree of comminutation of the plant material prior to the extraction process should provide sufficient particulate surface area for the extraction solvent to contact.

In a preferred embodiment, the extraction process (step 5, FIG. 1) is accomplished by placing fresh or dried plant material in an appropriate amount of extraction solvent to form a crude extract. In one preferred embodiment, the extraction solvent comprises an aqueous solution comprising about 0-95% ethanol in water or 0-100% methanol in water. The plant material is contacted with the extraction solution for an appropriate amount of time at a temperature between about room temperature and 75° C., preferably 40° C., to form the crude extract. The amount of plant material to extraction solvent used in the extraction process varies between about 2:1 to about 1:20, on a gram to milliliter basis, with about 1:4 to 1:8 being preferred. The crude extract contains both the desired anthocyanins as well as extraneous materials (e.g., plant sterols, fatty acids, triglycerides, sugars, organic acids, and other types of flavonoid glycosides) dissolved in the extraction solvent. The plant solids contained in the crude extract are separated from the liquid portion and the plant solids are either re-extracted as described above or discarded.

In one embodiment of step 5 (FIG. 1), pectinase is added either to the plant material or to the extraction solvent before or during the extraction process. Alternatively, the pectinase can be added to the crude extract after the extraction process is complete. The pectinase serves to prevent the extract from gelling at any point during or after the extraction process so that it will remain flowable during column purification. The amount of pectinase added will depend, of course, on the amount of plant material used to prepare the extract. Typically, the pectinase is added in an amount between about 0 and 0.12% by weight of the starting plant material.

Step 10 (FIG. 1) of the two column purification process of this invention comprises adding bisulfite ions ($HSO_3^-$) to the crude extract to form an extract containing anthocyanin-bisulfite adducts. Anthocyanins are positively charged molecules and therefore react with the negatively charged bisulfite ions, while flavonoid glycosides also present in the crude extract do not react with the bisulfite ions. The bisulfite ions can be added in any convenient manner, such as by the addition of sodium metabisulfite, sodium bisulfite, sulfurous acid, $SO_2$ gas, and the like. In one embodiment, sodium metabisulfite is dissolve in water and added to the crude extract. The amount of bisulfite ions added is preferably between about 10-20 equivalents, with 15 equivalents being preferred. The crude extract now comprises the anthocyanin-bisulfite adducts along with the extraneous materials mentioned above dissolved in the extraction solution. Formation of the anthocyanin-bisulfite adducts allows for the separation of the anthocyanins from the non-complexed neutral compounds present in the crude extract as described below.

If an alcoholic extraction solution was used to prepare the crude extract in step 5 (FIG. 1), the sulfited crude extract is concentrated in step 20 until it contains less than six percent alcohol, preferably while maintaining a temperature of 40° C. or less during the concentration. Water is added to dilute the concentrated, sulfited crude extract, and the diluted sulfited crude extract is either concentrated and diluted again with water prior to step 30, or is carried on directly to step 30 without performing a second dilution. Of course, if water was used as the extraction solution in preparation of the crude extract, the concentration step 20 is not necessary, and in this case the crude extract from step 10 is taken directly on to step 30 as shown by the dashed arrow in FIG. 1.

Step 30 (FIG. 1) of the two-column process comprises filtering the sulfited crude extract from step 20 to remove solids that may have precipitated from the crude extract. Filtration step 30 comprises adding a measured amount of a filter aid to the crude extract from step 20. Examples of suitable filter aids include diatomaceous earth and cellulose. The mixture of crude extract and filter aid is preferably shaken or stirred until homogeneous. The mixture is filtered through a bed of filter aid, and the bed is washed with deionized water.

The sulfited, filtered extract, which is at a pH of approximately 3.5, is then purified in the first purification step (step 40, FIG. 1) of the two-column process of this invention. In step 40, the sulfited, filtered extract from step 30 is contacted with an adsorbent material or resin which adsorbs non-complexed flavonoid glycosides, plant sterols, fatty acids and triglycerides, but absorbs very little of the anthocyanin-bisulfite adduct contained in the sulfited, filtered extract. Resins used in the first resin-contacting step 40 are non-ionic, reversed phase cross-linked resins. Among the non-ionic materials useful as adsorbents for the first purification step 40 include any of the known macroporous cross-linked polymers obtained by polymerization of styrene, divinylbenzene, trivinylbenzene, alkylvinylbenzene, acrylvinylbenzene, methyl methacrylate, and the like. In one preferred embodiment, the resin is a polymethacrylate resin such as CG-71cd Amberchrom (TosoHaas; Montgomery, Pa.). Generally about one liter of resin is needed per 100 grams of total anthocyanins present in the sulfited, filtered extract. While the steps of contacting crude or partially purified extracts with a resin are described herein in terms of contacting the extracts with a resin that is loaded into a column, such a description is merely for ease of explanation. Thus, the resin need not be packed into a column in order to perform the methods of this invention.

In one embodiment, the first resin of step 40 (FIG. 1) is packed in a column, and the sulfited, filtered extract is passed through the first resin at a rate of about one-half to one column volume per minute. That is, during step 40 the anthocyanin-bisulfite adduct passes through the resin, while undesired extraneous materials such as non-complexed flavonoid glycosides, plant sterols, fatty acids and triglycerides are retained by the resin. After all the sulfited, filtered extract has passed through the resin, the resin is washed with about 10 column volumes of deionized water to elute the remainder of the anthocyanin-bisulfite adduct. The load eluent and the water eluent from step 40 are combined to provide a first purified extract product, which comprises the anthocyanin-bisulfite adduct as well as sugars, salts, organic acids, and various phenols present in the plant material, in addition to anthocyanins which were not retained by the resin.

The first purified extract product from step 40 containing the anthocyanin-bisulfite adduct is acidified with mixing in step 50 (FIG. 1) to about pH 1.0 to 1.25 by the addition of concentrated sulfuric acid. The acid functions to break the anthocyanin-bisulfite adduct to provide uncomplexed anthocyanins. The acidified solution in step 50 is concentrated by partial evaporation to remove sulfur dioxide ($SO_2$) released from the adduct during acidification. The acidified solution from step 50 is then carried on to step 60 for the second purification of the extract.

The purpose of the second purification step (step 60, FIG. 1) is to separate the anthocyanins from sugars, salts, and organic acids still present in the acidified solution from step 50 (FIG. 1). Conventional methods used to achieve this level of purification typically involve extracting the anthocyanins into a polar organic solvent, for example by extracting the acidified solution numerous times with a solvent such as butanol or amyl alcohol. However, extractions with butanol or amyl alcohol are undesirable for many reasons, including the fact that such solvents have high boiling points and therefore are difficult to remove by evaporation. In addition, such solvents are classified as irritants and thus have special disposal requirements. Therefore, purifying anthocyanins by performing butanol or amyl alcohol extractions is not a desirable or efficient process where disposal considerations of such solvents play an important role in the overall feasibility of the process.

In step 60 (FIG. 1) of the present invention, the acidified solution from step 50 comprising the uncomplexed anthocyanins is contacted with a second adsorbent material or resin. The second resin used in step 60 is capable of adsorbing the uncomplexed anthocyanins but retains very little of the undesired extraneous materials remaining in the acidified solution. The present inventors discovered an efficient and economical process for obtaining a high purity anthocyanin composition by purifying the acidified solution from step 50 on a column by contacting the acidified solution with a brominated polystyrene resin, such as SP207 (Supelco; Bellafonte, Pa.), manufactured by Mitsubishi Chemical America. SP207 resin is a macroporous, brominated styrenic polymeric bead type resin designed for reversed-phase chromatographic applications, and has a particle size distribution between about 250-600 microns and a pore size range between about 100-300 Angstroms. The bromination of the aromatic rings provides increased hydrophobicity to the polystyrene resin, and is designed to provide a resin having increased selectivity for hydrophobic molecules relative to conventional styrene or divinylbenzene polymeric reversed-phase supports. Because of its tight binding properties, brominated polystyrene resin is not typically used in the purification of natural products. Thus, since it was known that conventional polystyrene resins tend to bind anthocyanins so tightly that it is very difficult to elute the anthocyanins from the polystyrene resin, it was expected that the brominated polystyrene resin would bind anthocyanins even tighter. Thus, it was not expected that a brominated polystyrene resin would be suitable for the purification of anthocyanins. However, the inventors surprisingly and unexpectedly discovered that the brominated polystyrene resin binds anthocyanins less tightly than non-brominated polystyrene resins, but still allows for the separation of anthocyanins from undesired extraneous impurities that are more polar than the anthocyanins.

To perform the purification step 60, the concentrated acidified product from step 50 is contacted with the brominated polystyrene resin, such as a resin which is packed into a column. When using a resin-packed column for purification step 60, generally about 40 grams of anthocyanins are loaded onto the column per liter of resin. Water dilution may be necessary if the solids concentration in the concentrated acidified product exceeds 200 grams per liter.

Subsequent to loading the acidified filtered extract onto the brominated polystyrene resin, undesired materials such as sugars, salts, and organic acids, which have little or no affinity for the adsorbent, are specifically washed from the resin with 0.1% aqueous acetic acid. Preferably about two column volumes of 0.1% aqueous acetic acid are used to elute the extraneous materials. The desired anthocyanins are then eluted from the resin using a polar organic solvent such as 50-75% ethanol/water or 50-100% methanol/water. Approximately four to ten column volumes of eluting solvent are required to elute the anthocyanins from the resin. Recovery of the anthocyanins from the eluent can be accomplished in any convenient manner such as by evaporation, distillation, freeze-drying, and the like, to provide an enriched extract of this invention.

The conditions employed in the two-column process of this invention provide extracts enriched for anthocyanins, wherein the blueberry extract final products contain at least 8% anthocyanins by weight of the extract. For example, in one embodiment, the enriched blueberry extract final product contains between about 8-40% by weight anthocyanins. In another embodiment, the enriched blueberry extract final product contains about 15% by weight anthocyanins. In certain embodiments, the enriched blueberry extract final product also contains at least 5% proanthocyanins.

The two-column method of this invention also provides bilberry extracts comprising at least 8% anthocyanins. In one embodiment, the bilberry extract contains between about 8-55% anthocyanins, more preferably between about 28% and 45% total anthocyanins. In some embodiments, the extracts also contain at least 5% proanthocyanins. The two-column method described above also advantageously allows for high loading on both the first and the second columns.

B. One-Column Purification Process

Figure 2:
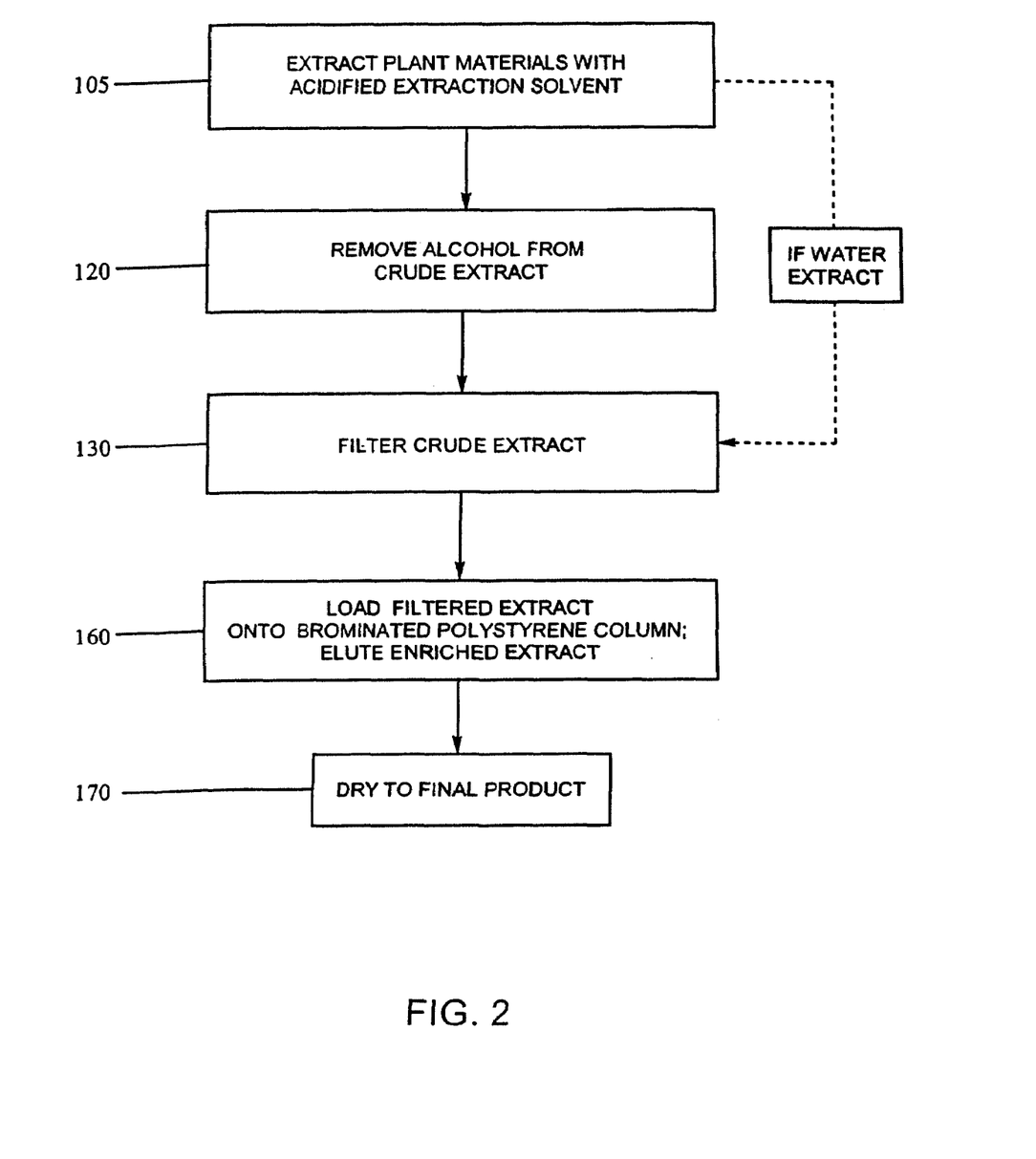
FIG. 2 is a flow chart for preparing an enriched extract according another embodiment of this invention comprising one purification of the extract.

FIG. 2 is a flow-chart showing the steps of a second embodiment of this invention in which a purified extract of this invention enriched for anthocyanins may be prepared by a one-column purification process. The one-column purification method of this invention provides compositions enriched in anthocyanins, wherein the compositions comprise suitable concentrations of total anthocyanins for use as nutraceuticals. While the presence of proanthocyanins is difficult to measure, it is believed that the compositions isolated from the one-column method also contain proanthocyanins. The one-column process of this invention allows for the elimination of the first column (step 40, FIG. 1) used in the two-column process described above. Further, the one-column method of this invention eliminates the sulfitation step (step 10, FIG. 1) of the two-column purification method of this invention, thus advantageously eliminating the need to use a sulfiting reagent and in turn eliminating the acidification step 50 (FIG. 1) of the two-column process. Thus, the one-column process of this invention provides an even more economical and efficient method of obtaining compositions enriched for anthocyanins by eliminating several process steps and by reducing the amount of reagents needed in the process, thereby reducing production costs and waste disposal issues.

In a preferred embodiment of the one-column process of this invention, as illustrated in steps 105-160 in FIG. 2, anthocyanins are extracted from a fresh or dried plant material (step 105, FIG. 2). As described in the two-column process, a variety of extraction methods are available in the literature, such as vat extraction, percolation, countercurrent extraction, etc. The particular method of extraction employed is not essential to the process of the present invention. The degree of comminutation of the plant material prior to the extraction process should provide sufficient particulate surface area for the extraction solvent to contact.

The extraction process (step 105, FIG. 2) is preferably accomplished by placing fresh or dried plant material in an appropriate amount of extraction solvent. In one preferred embodiment, the extraction solvent comprises an acidified alcohol solution having about 0-95% ethanol in water and a suitable acid in an amount of about 0.5-3%, more preferably about 0.5-1.0% by weight. In another preferred embodiment, the extraction solvent comprises an acidified alcohol solution having between about 0-100% methanol in water or between about 0-95% ethanol in water and between about 0.5-3% by weight of a suitable acid. Suitable acids that may be used in the extraction step include sulfuric acid ($H_2SO_4$) or hydrochloric acid (HCl). The plant material is contacted with the extraction solution for an appropriate amount of time at a temperature between about room temperature and 75° C., preferably at 40° C., to form the crude extract. The amount of plant material to extraction solvent used in the extraction process varies between about 2:1 to about 1:20 on a gram to milliliter basis, with about 1:4 to 1:8 being preferred. The crude extract contains anthocyanins (and most likely proanthocyanins) as well as extraneous materials such as plant sterols, fatty acids, triglycerides, and undesired compounds that are more polar than the anthocyanins, dissolved in the extraction solvent. The solid residue contained in the crude extract is separated from the liquid portion and the residue is either re-extracted as described above or discarded.

In one embodiment of step 105 (FIG. 2), pectinase is added either to the plant material or to the extraction solvent before or during the extraction process. Alternatively, the pectinase can be added to the crude extract after the extraction process is complete. The pectinase serves to prevent the extract from gelling at any point during or after the extraction process so that it will remain flowable during column purification. The amount of pectinase added will depend, of course, on the amount of plant material used to prepare the extract. Typically, the pectinase is added in an amount between about 0 and 0.12% by weight of the plant material.

If either an ethanolic or methanolic extraction was used to prepare the crude extract, the crude extract is concentrated until the crude extract contains less than 6% ethanol or methanol, preferably maintaining a temperature of 40° C. or less during concentration. Water is added to dilute the concentrated crude extract, and the diluted crude extract is either concentrated and diluted again with water prior to step 130, or is carried on directly to step 130 without performing a second dilution. Of course, if water was used as the extraction solution in preparation of the crude extract, step 120 is not necessary, and in this case the crude extract from step 105 is taken directly on to step 130 as shown by the dashed arrow in FIG. 2.

Step 130 (FIG. 2) of the one-column process comprises filtering the crude extract from step 120 to remove solids that may have precipitated from the crude extract. The inventors discovered that the amount of undesirable, extraneous compounds that precipitate from the extraction solution could be increased by adjusting the extraction conditions in step 105. The precipitated extraneous compounds can then be easily removed by filtration in step 130. Various filtration methods may be employed in filtration step 130 of the one-column process of this invention. One filtration method that may be employed in step 130 comprises adding a measured amount of a filter aid such as diatomaceous earth or cellulose to the crude extract. The mixture of crude extract and filter aid is preferably shaken or stirred until homogeneous, and then the mixture is filtered through a bed of filter aid. The bed is washed with an aqueous acidic solution, preferably about 1% aqueous sulfuric acid.

Other filtration methods that may be used in step 130 include filtering the crude extract through sand or through a 30-micron polypropylene filter that is preferably plugged with glass wool. Yet another filtration method comprises using a bag filter (a bag-shaped cloth filter composed of polyethylene or polypropylene), which may advantageously be placed in-line with the purification column of step 160 described below.

In step 160 (FIG. 2), the filtered extract from step 130 comprising the desired anthocyanins and the undesired extraneous compounds is contacted with a brominated polystyrene adsorbent material or resin capable of adsorbing the anthocyanins (and the proanthocyanins). As discussed above in the two-column process, the inventors surprisingly and unexpectedly discovered that the brominated polystyrene resin binds anthocyanins less tightly than non-brominated polystyrene resin while still allowing clean separation of the anthocyanins from undesired extraneous compounds such as sugars, salts, and organic acids. Again, while the steps of contacting crude or partially purified extracts with a resin are described herein in terms of contacting the extracts with a resin packed into a column, such a description is merely for ease of explanation. Thus, the resin need not be packed into a column in order to perform the method of this invention.

In one embodiment of the purification step 160, the filtered crude extract from step 130 is loaded onto a column packed with brominated polystyrene resin having a particle size distribution between about 250-600 microns and a pore size range between about 100-300 Angstroms. The amount of crude extract that is loaded onto the column depends on the plant material used to prepare the crude extract. For example, when the crude extract is prepared from bilberry, about 16-30 grams of anthocyanins may be loaded per liter of resin. When the crude extract is prepared from blueberry, about 9-25 grams of anthocyanins may be loaded per liter of resin. The crude extract may be diluted with water prior to loading if the solids concentration in the concentrated crude extract exceeds 200 grams per liter of crude extract.

Subsequent to loading the filtered crude extract onto the resin, undesired materials such as sugars, salts, and organic acids, which have little or no affinity for the adsorbent, are specifically washed from the resin with 0.1% aqueous acetic acid. Preferably about two column volumes of 0.1% aqueous acetic acid are used to elute the extraneous materials. The desired anthocyanins (and the proanthocyanins) are then eluted from the resin using a polar organic eluting solvent such as 50-75% ethanol/water or 50-100% methanol/water. Approximately four to ten column volumes of eluting solvent are required to elute the anthocyanins from the resin. Recovery of the anthocyanin from the eluent can be accomplished in any convenient manner such as by evaporation, distillation, freeze-drying, and the like, to provide an enriched extract of this invention.

The above-described one column process is suitable for preparing compositions sufficiently enriched for anthocyanins for use as nutraceuticals from a variety of plant materials that contain anthocyanins, such as blueberries, bilberries, blackberries, strawberries, red currants, black currants, cranberries, cherries, raspberries, grapes, currants, elderberries, hibiscus flowers, bell peppers, red cabbage, purple corn, and violet sweet potatoes. For example, when enriched extracts were prepared from dried bilberry, the enriched bilberry extract final product prepared using the one-column process of this invention contained at least 8% by weight total anthocyanins. For example, in one embodiment the enriched bilberry extract final products contain about 8-50% by weight total anthocyanins. In another example, enriched extracts were prepared from dried blueberries using the one-column process of this invention, the enriched blueberry extract final products prepared using the one-column process of this invention comprised between about 8-35% total anthocyanins. As stated above, many of the plant materials that contain anthocyanins also contain other phenolic compounds as well. Therefore, the enriched extract final products of this invention may also contain at least 20% total phenols. By "total phenols," it is meant the total amount of all the various phenolic compounds isolated in the enriched extract prepared by the method of this invention. The types of phenolic compounds present in plant materials used in the method of this invention are well known to those skilled in the art and need not be described further.

If it is desired to further purify the enriched extracts obtained by either the two-column process or the one-column process of this invention, the enriched extracts described above may be contacted with an anion exchange resin to remove organic acids which may still be present in the enriched extract. Anion exchange media suitable for further purification of the enriched extracts include weak anion exchange resins, for example, a diethylaminoethanol resin such as DEM-63 (Whatman) or Toyopearl DEAE-650M (TosoHaas). Alternatively, a strong anion exchange resin may be used to further purify the enriched extracts of this invention. Examples of strong anion exchange resins include quaternary amine resins such as Super Q-650M (TosoHaas). Preferably, the anion exchange resin is a weak anion exchange resin. To perform the anion exchange column purification, the enriched extract is dissolved in water and contacted with the anion exchange resin, which may be packed in a column. The resin is washed with water to elute the further enriched extract. Using the additional anion exchange resin purification step, an enriched extract containing about 24% total anthocyanins isolated from dried blueberries was further enriched to about 38% total anthocyanins.

Figure 3:
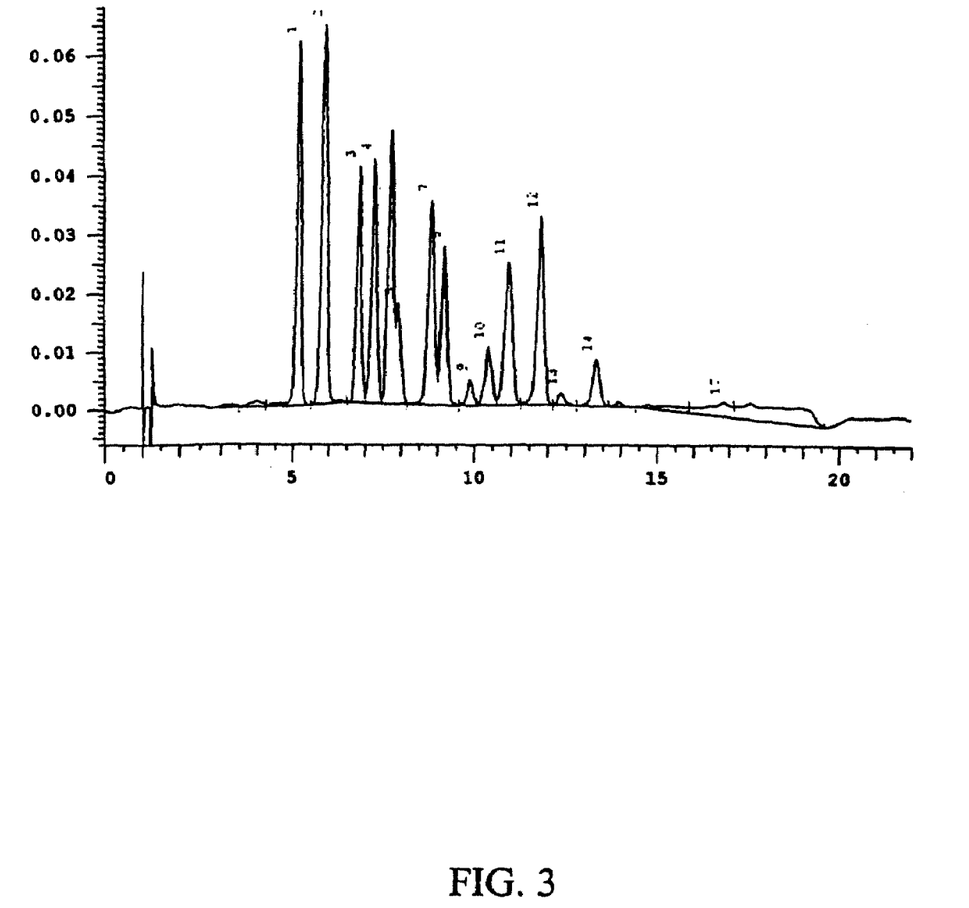
FIG. 3 is an HPLC chromatogram of an enriched bilberry extract final product at 510 nm.
Figure 4:
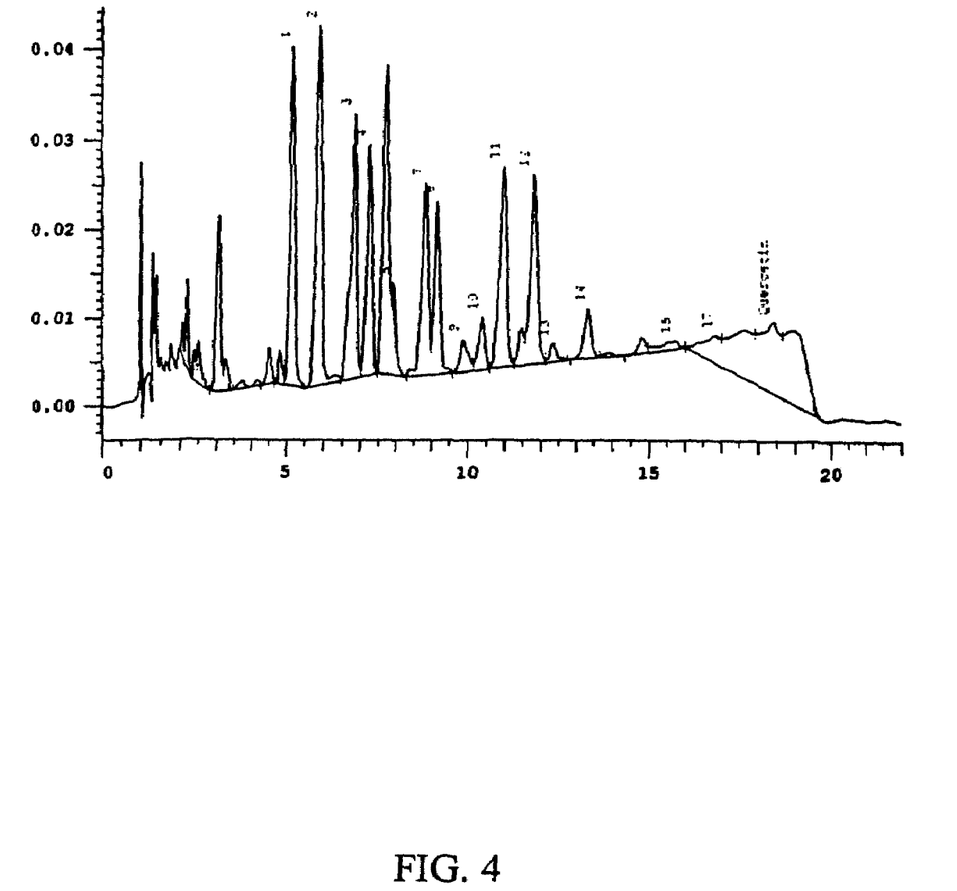
FIG. 4 is an HPLC chromatogram of an enriched bilberry extract final product at 280 nm.

FIGS. 3 and 4 are HPLC chromatograms of bilberry extracts prepared according to the one column process at 510 nm and 280 nm, respectively. Table 1 summarizes the percent of each anthocyamide in the final bilberry extract identified by the HPLC of FIG. 3.

TABLE 1

Percent anthocyanides in bilberry extract

| NAME | PEAK # | PERCENT COMPOSITION |
| --- | --- | --- |
| Delphinidin-3-O-galactoside | 1 | 3.3 |
| Delphinidin-3-O-glucoside | 2 | 3.9 |
| Cyanidin-3-O-galactoside | 3 | 2.1 |
| Delphinidin-3-O-arabinoside | 4 | 2.6 |
| Cyanidin-3-O-glucoside | 5 | 2.8 |
| Petunidin-3-O-galactoside | 6 | 1.0 |
| Petunidin-3-O-glucoside | 7 | 2.5 |
| Cyanidin-3-O-arabinoside | 8 | 1.7 |
| Peonidin-3-O-galactoside | 9 | 0.3 |
| Petunidin-3-O-arabinoside | 10 | 0.8 |
| Malvidin-3-O-galactoside Peonidin-3-O-glucoside | 11 (co-elute) | 2.1 |
| Malvidin-3-O-glucoside | 12 | 2.5 |
| Peonidin-3-O-arabinose | 13 | 0.1 |
| Malvidin-3-O-arabinose | 14 | 0.6 |
| Total | | 26.3 |

Figure 5:
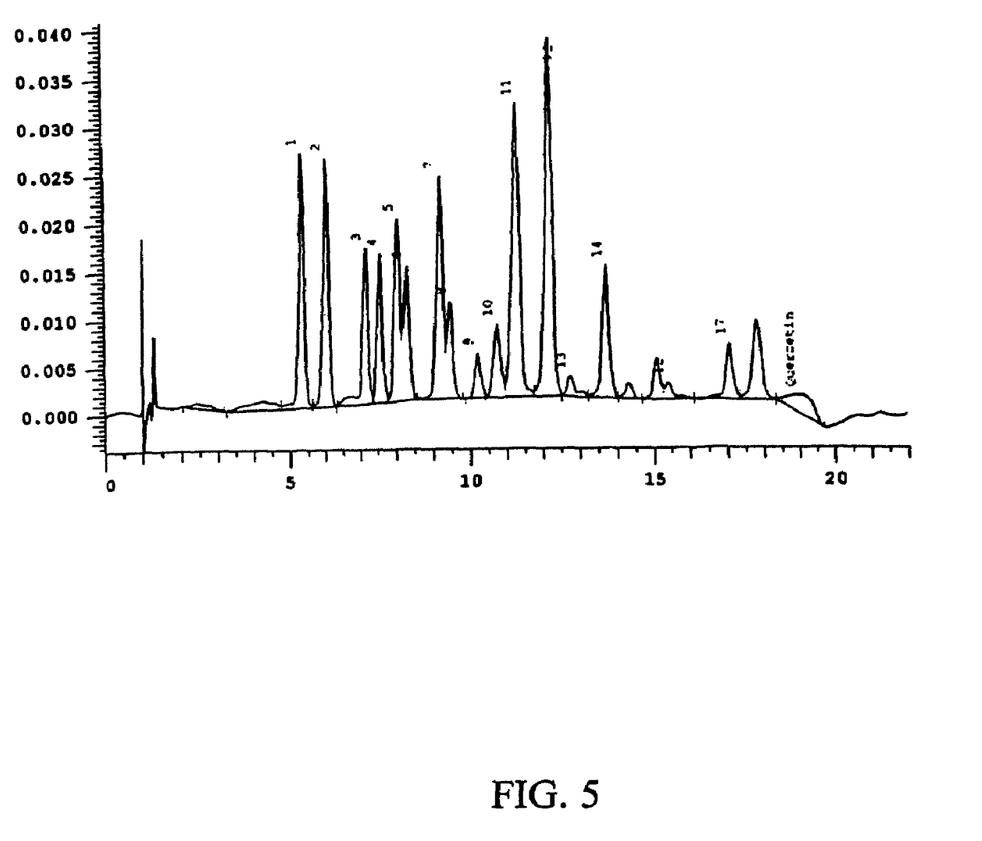
FIG. 5 is an HPLC chromatogram of an enriched blueberry extract final product at 510 nm.
Figure 6:
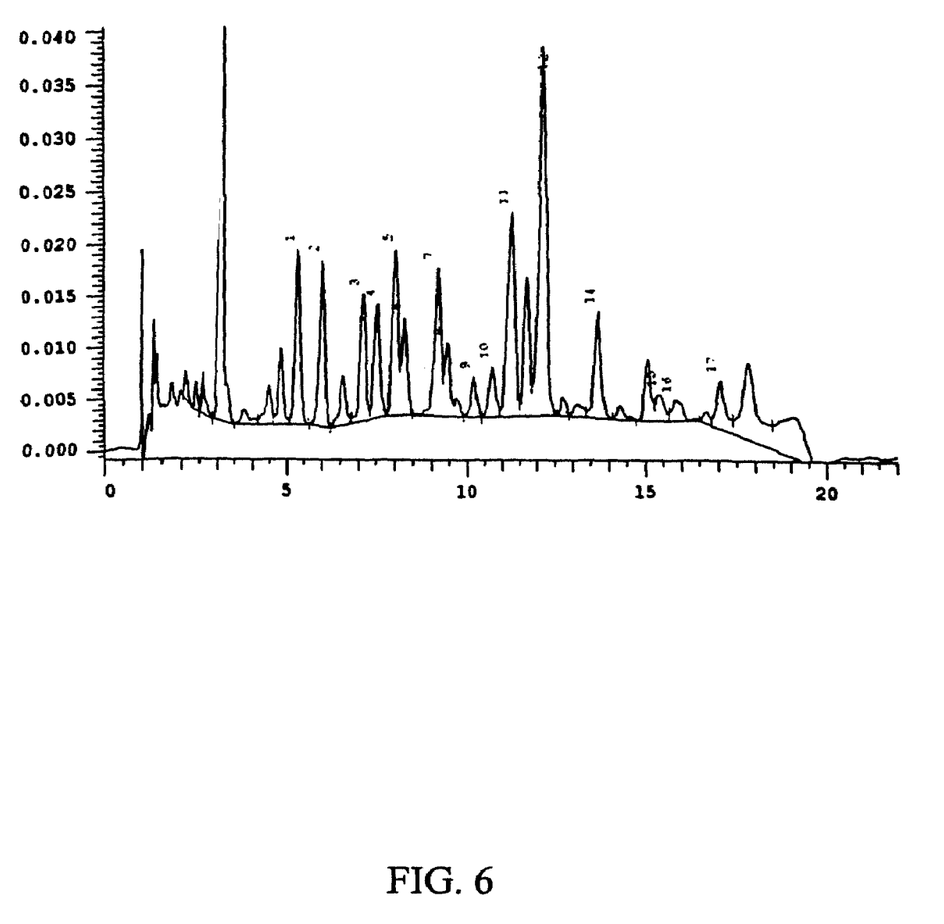
FIG. 6 is an HPLC chromatogram of an enriched blueberry extract final product at 280 nm.

FIGS. 5 and 6 are HPLC chromatograms of blueberry extracts prepared according to the one column process at 510 nm and 280 nm, respectively.

The enriched extracts of this invention may be formulated as pills, capsules, or tinctures. In formulating compositions according to this invention, a wide range of excipients may be used, the nature of which will depend, of course, on the intended mode of application of the composition. Examples of excipients include preservatives, carriers, and buffering, thickening, suspending, stabilizing, wetting, emulsifying, coloring and flavoring agents, and in particular carboxy vinyl polymers, propylene glycol, ethyl alcohol, water, cetyl alcohol, saturated vegetable triglycerides, fatty acid esters or propylene glycol, triethanolamine, glycerol, starch, sorbitol, carboxymethyl cellulose, lauryl sulphate, dicalcium phosphate, lecithin, etc.

The enriched extracts of this invention may be used as dietary supplements (e.g., dietary antioxidants) and for the treatment of disorders in humans and mammals. For example, the enriched extracts of this invention may be used for improving visual acuity and for treating circulatory disorders, diabetes, and ulcers. In addition, the enriched extracts may be used as anti-inflammatory agents, antiviral agents, and antimicrobial agents.

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

EXAMPLES

Example 1

One-Column Process Purification of Bilberry with Water Extraction

Three extractions were performed on 1 kg of dried Bilberry raw material. One extraction used 6 L of water and the other two extractions used 4 L of water. All extractions were acidified to 5 g/L sulfuric acid. There was about an 88% recovery of anthocyanins into the extract. Exactly 2.3 L of the crude extract were filtered through a polypropylene 30-micron filter, with a layer of glass wool over the filter. The glass wool was changed once and the filter rinsed off with deionized water. The final volume of the filtrate was 2.43 L with a 90.9% recovery of anthocyanins in the filtrate.

A column was packed with brominated polystyrene resin SP207 (Supleco; Belefonte, Pa.) and equilibrated with 0.1% acetic acid. The column was loaded with 2.24 L of filtrate at a solids concentration of 29.8 g/L and a flow rate of 2.2 mL/min. The loading bleed was less than 0.9% with an overall loss of 4.07% of the anthocyanins in the loading and first two column washes. There was an 88.4% recovery of the anthyocyanins in the elution step and an anthocyanins mass balance of 92.5%. A few hundred milliliters of elution product was evaporated to dryness on a rotary evaporator and then lyophilized. Final assay was by standard spectrophotometric determination of absorbance at 535 nm against a delphinidin chloride standard (102 absorbance units/g/L at 1.0 cm) of dried product. The enriched composition contained 43% by weight total anthocyanins.

Example 2

One-Column Process Purification of Bilberry with 70% Ethanol Extraction

Dried bilberry biomass (667 g), assayed at 2.0% anthocyanins, was extracted by percolation using 70% ethanol/water containing 3% sulfuric acid. The crude extract contained 3.9% total anthocyanins. One liter of the first extraction volume was mixed with 100 mL deionized water and evaporated in vacuo to about 460 mL. Deionized water (300 mL) was added to the mixture, and an additional 170 mL of liquid was evaporated. Deionized water (210 mL) was added to make the final volume 800 mL. To the aqueous mixture was added 150 g Celite 512 (0.5 to 0.9 grams Celite per gram of solids). The mixture was shaken until homogeneous. The Celite/extract mixture was poured over a 30 g bed of damp Celite 512 under vacuum. Upon completion of filtration, the bed was washed with 1.20 L of 1% aqueous sulfuric acid in 200 mL increments. The filtrate volume was 1855 mL. To the filtrate was added 145 mL deionized water to give a final volume of 2.0 L. The filtrate was loaded at 2.2 mL/minute (1.3 mL/cm$^2$/min) onto a column loaded with 170 mL brominated polystyrene resin (Supleco). The amount loaded was 695 mL, giving a load value of 17 g of anthocyanins per liter of column media. The column was washed with one column volume of 0.1% aqueous acetic acid and with 2.5 column volumes of 0.1% HOAc/10% ethanol/90% water. Anthocyanins were eluted with 10 column volumes of 70% ethanol/water. The product was evaporated in vacuo at 60° C. and 50 mbar to a black, dry, shiny amorphous solid. Final assay was by standard spectrophotometric determination of absorbance at 535 nm against a delphinidin chloride standard (102 absorbance units/g/L at 1.0 cm) of dried product. The enriched extract was assayed as containing 32% total anthocyanins purity by weight.

Example 3

Two-Column Purification of Bilberry

Dried bilberry (1.00 kg) was ground to approximately 2 mm in a Wiley mill. The ground biomass was weighed into a 10 L round bottom flask. To the flask was added 4.00 L of 90% ethanol/water. The mixture was put on a rotary evaporator, rotated at 90 rpm at atmospheric pressure and kept at a temperature of 74° C. for four hours. The mixture was cooled to room temperature filtered through Whatman #1 paper and stored. Exactly 2.0 L of the extract was mixed with 150 mL deionized water containing 17.1 g sodium metabisulfite, concentrated on a rotary evaporator to 500 mL, diluted to 750 L with deionized water, concentrated on a rotary evaporator to 400 mL, and diluted to a final volume of 1200 mL with deionized water. To the diluted mixture was added 110 g Celite 512. The suspension was mixed thoroughly and filtered through a bed of Celite 512. The filter cake was washed with 500 mL of deionized water.

The sulfited, filtered extract was loaded onto a polymethacrylate column (CG-71 cd Amberchrom; (TosoHaas; Montgomery, Pa.), column volume 60 mL, at a rate of 30 mL per minute. The column was eluted with 600 mL deionized water and cleaned with methanol. The load eluent and the water eluent were combined to give the first column product.

The first column product was acidified to pH 1 with sulfuric acid, concentrated on a rotary evaporator to remove sulfur dioxide, and loaded onto a column loaded with 80 mL brominated polystyrene resin (Supleco). Loading was continued until anthocyanin bleeding was severe. The column media was then washed with about 400 mL 0.1% aqueous HOAc and anthocyanins were eluted with 12 column volumes of methanol. Final assay was by standard spectrophotometric determination of absorbance at 535 nm against a delphinidin chloride standard (102 absorbance units/g/L at 1.0 cm). Solids were determined by gravimetric residue. The enriched extract was assayed at 41.6% total anthocyanins purity by weight.

Example 4

Enriched Extracts from Blueberry Biomass

To 940 g of dried and ground blueberry (Van Drunen FutureCeuticals; Momence, Ill.) were added 4.0 liters of extraction solvent (1.0% w/v sulfuric acid/70% aqueous ethanol) in a 10 L round bottom flask. The flask was rotated in a constant temperature water bath held at 40° C. for two hours. The mixture was swirled and filtered through a 150 g bed of Celite 512 under vacuum. The blueberry biomass cake was washed with 500 mL of extraction solvent. The cake was carefully scraped away from the Celite bed, poured into a round bottom flask, and re-extracted following the above-described procedure. A third extraction was then performed. The three crude extracts were combined.

The combined extracts (2.00 L) were evaporated in vacuo to 175 mL at an external temperature of 40° C. The evaporated extract was diluted with deionized water to give 675 mL of crude blueberry extract. The crude extract was loaded without filtration onto a previously conditioned (i.e., washed with acetone) and equilibrated column loaded with 170 L brominated polystyrene resin (Supleco). The column was washed with 0.1% aqueous acetic acid and with 0.1% aqueous HOAc/ 10% aqueous ethanol. The anthocyanins were then eluted with 70% aqueous ethanol. The product pool was evaporated in vacuo at 50 mbar pressure and 60° C. Final assay was by standard spectrophotometric determination of absorbance at 535 nm against a delphinidin chloride standard (102 absorbance units/g/L at 1.0 cm). The purified blueberry extract was assayed at 18% total anthocyanins purity by weight, and overall recovery of anthocyanins was 95%.

Example 5

Purification of an Enriched Blueberry Extract

In this example, portions of an enriched blueberry extract having 18% by weight total anthocyanins, prepared as described in Example 4, were passed through either a strong or a weak anion exchange resin to remove residual acids to increase the purity of the enriched extract.

Approximately 1.0 g of the enriched blueberry extract was dissolved in 50 mL of water and passed through a 9 mL column containing either a strong anion exchange resin (Super Q-650 M; TosoHaas; Montgomery, Pa.) or a weak anion exchange resin (DEM-63; Whatman). The column was washed with 30-35 mL of water. In the case of the strong anion exchange resin column, the resin was further washed with 25 mL of 20% ethanol and then with 40% ethanol. The composition isolated from the strong anion exchange column contained 28.3% by weight total anthocyanins and the recovery was 88%. The composition isolated from the weak anion exchange column contained 30.6% by weight total anthocyanins and the recovery was 88%.

Example 6

Enriched Extracts from Bilberry Biomass Using Pectinase Treatment

To 1024 g of frozen bilberries was added 548 g of warm water. The mixture was pureed in a blender and then heated to 40° C. After this, 150 µL of pectinase (Quest Super 7x) were added for a 30-minute treatment at 40° C. while stirring. Approximately 4 mL of sulfuric acid were mixed into the slurry to achieve an acid concentration of 0.5%. The mixture was then heated to 45° C. and extracted for 15 minutes under very slow stirring. To the extracted mixture was added 164 g of Dicalite, which was then filtered over a 26 g Dicalite bed. The cake was washed with 400 mL of warm 0.1% aqueous sulfuric acid three times. This extract was filtered through a 25 µm pressure filter. All of the filtered extract (2.4 L) was loaded onto a SP-207 column (0.96 meter, 170 mL). After loading, the column was washed with 0.1% aqueous acetic acid and then eluted with 70% aqueous ethanol. The column product was evaporated to dryness and then placed on a lyophilizer for 48 hours. The final product was assayed for total anthocyanins by standard spectrophotometric determination of absorbance at 535 nm. The purified bilberry extract was assayed to contain 40% total anthocyanins purity by weight. The overall recovery was approximately 79% for anthocyanins.

We claim:

1. A purified bilberry extract, comprising about 8-55% anthocyanins by weight of said extract, wherein during the process of making said extract no bisulfite ions are added, said extract comprising delphinidin-3-O-galactoside, delphinidin-3-O-glucoside, cyanidin-3-O-galactoside, delphinidin-3-O-arabinoside, cyanidin-3-O-glucoside, petunidin-3-O-galactoside, petunidin-3-O-glucoside, cyanidin-3-O-arabinoside, peonidin-3-O-galactoside, petunidin-3-O-arabinoside, malvidin-3-O-galactoside/peonidin-3-O-glucoside, malvidin-3-O-glucoside, peonidin-3-O-arabinose, and malvidin-3-O-arabinose.

2. The bilberry extract according to claim 1, comprising 3.3% delphinidin-3-O-galactoside, 3.9% delphinidin-3-O-glucoside, 2.1% cyanidin-3-0-galactoside, 2.6% delphinidin-3-O-arabinoside, 2.8% cyanidin-3-O-glucoside, 1.0% petunidin-3-O-galactoside, 2.5% petunidin-3-O-glucoside, 1.7% cyanidin-3-O-arabinoside, 0.3% peonidin-3-O-galactoside, 0.8% petunidin-3-O-arabinoside, 2.1% malvidin-3-O-galactoside/peonidin-3-O-glucoside, 2.5% malvidin-3-O-glucoside, 0.1% peonidin-3-O-arabinose, and 0.6% malvidin-3-O-arabinose.

* * * * *